United States Patent [19]

Pratt

[11] Patent Number: 5,078,843
[45] Date of Patent: Jan. 7, 1992

[54] METHOD FOR FABRICATING HIGH-TEMPERATURE TENSILE TEST SPECIMENS

[75] Inventor: Wilson N. Pratt, Anaheim, Calif.

[73] Assignee: General Dynamics Corporation Air Defense Systems Division, Pomoma, Calif.

[21] Appl. No.: 365,305

[22] Filed: Jun. 13, 1989

Related U.S. Application Data

[62] Division of Ser. No. 173,787, Mar. 28, 1988, Pat. No. 4,895,750.

[51] Int. Cl.$^5$ .......................... C25D 7/00; C25D 5/02
[52] U.S. Cl. .................................. 205/118; 205/150; 205/274
[58] Field of Search ........................ 204/29, 24, 15; 427/282, 292

[56] References Cited

U.S. PATENT DOCUMENTS

| | | | |
|---|---|---|---|
| 2,454,850 | 11/1948 | Van Winkle et al. | 73/99 |
| 2,984,604 | 5/1961 | Duva et al. | 204/47 |
| 3,426,587 | 2/1969 | Schmieder | 73/103 |
| 3,536,460 | 10/1970 | Voelker | 73/103 |
| 3,572,091 | 3/1971 | McFarland | 73/760 |
| 3,761,231 | 9/1973 | Dowell et al. | 428/81 |
| 3,826,155 | 7/1974 | Muller | 156/309 |
| 3,842,664 | 10/1974 | Conway, Jr. | 73/760 |
| 4,078,417 | 3/1978 | Shigekawa | 73/1 R |
| 4,344,995 | 8/1982 | Hammer | 428/61 |
| 4,398,659 | 8/1983 | Richter | 428/367 |
| 4,409,841 | 10/1983 | Archer | 73/760 |
| 4,479,991 | 10/1984 | Thompson | 428/76 |
| 4,522,889 | 6/1985 | Ebneth et al. | 428/614 |
| 4,599,255 | 7/1986 | Anglin et al. | 428/73 |
| 4,603,071 | 7/1986 | Wehnert et al. | 428/112 |
| 4,610,157 | 9/1986 | Vicki et al. | 73/1 R |
| 4,684,560 | 8/1987 | Minten et al. | 428/131 |

OTHER PUBLICATIONS

F. A. Lowenheim, *Electroplating*, McGraw-Hill Book Co., New York, 1978, pp. 205-224.

Primary Examiner—John T. Niebling
Assistant Examiner—William T. Leader
Attorney, Agent, or Firm—Henry Bissell; Leo R. Carroll

[57] ABSTRACT

A carbon composite tensile test specimen for high temperature testing and a method of fabricating the same are disclosed. A plurality of holes are drilled in first and second end sections of the specimen and then the end sections are electroplated with nickel. The nickel plating of the end sections prevents breakage of the ends in the jaws of a tensile testing apparatus. For high-temperature testing, a standard-sized specimen may be used with the jaws in the hot zone.

6 Claims, 1 Drawing Sheet

METHOD FOR FABRICATING HIGH-TEMPERATURE TENSILE TEST SPECIMENS

This is a division of application Ser. No. 07/173,787, filed Mar. 28, 1988 now U.S. Pat. No. 4,895,750.

REFERENCE TO RELATED APPLICATION

The present application is related to an application entitled "A Method For Attaching Carbon Composites to Metallic Structures and Product Thereof," of W. N. Pratt et al, filed concurrently herewith and assigned to the assignee of the present application.

BACKGROUND OF THE INVENTION

1. Field of the Invention.

The present invention relates to tensile test specimens of carbon composite materials and methods for fabricating the same. In particular, the present invention relates to a method of providing a tensile test specimen with end portions having improved strength for carrying out high-temperature tensile testing.

2. Description of the Related Art.

Composite materials produced by embedding fibers in the form of staple, filament, or yarn in a matrix of plastic, metal, or ceramic have found many uses in engineering applications requiring high strength and low weight, as in aeronautics and astronautics. Fibers retaining high strength at elevated temperatures are valuable in high-temperature applications. Carbon and graphite fibers fall into this category. Because the element carbon has the ability to form strong bonds between its atoms, carbon atoms are capable of holding together in strings to form long unidimensional polymer structures in the same way that molecules form the basic structural units of fibers. The fibers used in textiles are based almost exclusively on organic polymers consisting of long chains of carbon atoms with other atoms or groups of atoms attached as appendages to the carbon "spine." By removing the appendages from an organic fiber molecule, long molecules consisting entirely of carbon atoms can be produced. When chemical stripping of the appendages is carried out on a highly oriented organic fiber, carbon fibers in which the molecules have a high degree of orientation can be obtained. Carbon fibers of this sort may be produced by subjecting organic fibers to pyrolysis. Carbon fibers are formed at lower temperatures; at higher temperatures the carbon atoms in the fiber are arranged in the crystalline form of graphite.

Carbon fibers have a high strength-to-weight ratio and retain high strength at temperatures at which other engineering materials suffer significant loss of strength. Composite materials containing carbon fibers have many uses in the construction of aircraft and spacecraft.

The determination of the tensile strength of a given material is ordinarily carried out by mounting an elongated specimen of known cross section in a testing apparatus which grips the ends of the specimen and subjects it to a known tensile force. The ends of the specimen are normally shaped to suit the requirements of the particular gripping arrangement utilized in the testing apparatus. The elastic properties and the ultimate yield strength of the material are determined experimentally by the application of calibrated force values to the specimen of known cross sectional area. Generally the specimen under test has end portions of larger cross section than a narrowed central part, so that failure of the specimen occurs somewhere in the central part. In the case of testing at high temperature of a carbon composite material, it has been found that the test specimen must be made long enough so that the ends are not inside the high-temperature zone. It has also been found that an end of a carbon composite test specimen being held in the test apparatus jaws will frequently break. It would be a beneficial advance in the art of carbon composite tensile testing if a way were found to make possible the use of standard-size test bars at high temperature without breakage at one of the ends.

Some examples of the related art are described briefly below.

U.S. Pat. No. 2,454,850 to van Winkle et al relates to an improved torsional specimen and means for mounting the same in a machine for testing the torsional characteristics of materials. The improved specimen comprises coaxial cylindrical end portions and a narrowed-down intermediate portion. Flats are ground on the cylindrical surfaces of the end portions to be engaged by t screws mounted in holder blocks of the testing apparatus.

U.S. Pat. No. 3,426,587 to Schmeider relates to a rupture test specimen and a coupling therefor. A coupling member with an aperture having a circular central cross section and elongated end cross sections is connected to a mating rod member with an enlarged end portion having a similar elongated cross section. Because the aperture is circular in the central part of the coupling member, the rod member is rotatable 90° to provide a positive coupling between the coupling member and the rod member.

U.S. Pat. No. 2,984,604 to Duva et al discloses a platinum plating composition and process. A platinum electrolyte is provided from which it is possible to plate thick layers of stress-free platinum by a process which is disclosed. The drawing reproduces a photomicrograph of a specimen of platinum plated graphite made according to the process.

U.S. Pat. No. 3,536,460 to voelker relates to a low-resistance joint assembly made between a carbon body and an electrical conductor. One assembly member contains an internally threaded recess and the other is externally threaded. An alloy within the recess between threads or the carbon body and threads of the conductor is melted and then cooled to solidify it between threads of the assembly members.

U.S. Pat. No. 3,761,231 to Dowell et al relates to a composite article for use, for example, as a functional block comprising a block of non-metallic material having embedded wherein a layer of porous material in the form of a three-dimensional network arranged so as to define a plurality of intercommuncating cellular spaces, the said layer extending adjacent one surface of the block but not wholly therethrough. The porous material may be metallic, in the form of a sheet produced by spraying, dipping, or electrodepositing of a metal on a polyurethane foam material, or alternatively, the porous material may be non-metallic, for example ceramic, or may be in the form of a three-dixensional fine gauge wire mesh or felt, or perforated sheet arranged in the form of a three-dimensional network, such as "expanded metal" sheet.

U.S. Pat. No. 4,344,994 to Hammer discloses a graphite-containing composite structure having a fastener area for joining the composite to other structures. The graphite-reinforced laminate terminates adjacent the fastener area. Kevlar-reinforced laminates about the graphite laminate and extend over the fastener area and are further reinforced with Kevlar laminates that overlap the graphite and extend over the fastener area.

U.S. Pat. No. 4,398,659 to Richter discloses a method of bonding a graphite fiber-reinforced glass matrix composite to a metal structure. The method comprises depositing a layer of eutectic alloy metal component to the bond surfaces of the metal and composite followed by placing the thus treated bond surfaces of the metal and composite together with a layer of eutectic alloy containing such metal therebetween. The metal-bond-composite is then heated to melt the alloy and bond the composite to the metal.

U.S. Pat. No. 4,479,991 to Thompson describes an electrically non-conductive board having thin layers of metal bonded to major surfaces thereof to form a laminate substrate. Axially aligned relief holes, each having a sidewall, are formed in each of the thin layers or metal of the laminate substrate. The laminate substrate and the relief holes are then coated and encapsulated with a plastic resin to form plastic-coated laminate.

U.S. Pat. No. 4,599,255 to Anglin et al discloses a fiberglass fabric wherein a selected number and pattern of yarns which have been coated with an aluminum coating is preimpregnated with epoxy or another resin system and is laid up as an integral part of a composite structure of the type having a honeycomb core and a plurality of fiberglass plies. Multiple plies of fiberglass fabric which include the yarns coated with an aluminum coating may be utilized in edge band fastener areas for increased electrical continuity without loss of mechanical strength of composite parts.

U.S. Pat. No. 4,684,560 to Minten et al relates to a process for preparing a non-conductive substrate for electroplating, and in particular to a process for preparing the through hole walls of a printed wiring board for electroplating. The process consists of preparing a liquid dispersion of carbon black particles, applying the dispersion to the surface of the non-conducting material, separating substantially all of the dispersing medium from the carbon black particles, and electroplating a substantially continuous conductive metal layer over the deposited carbon black layer. Other examples of related art are contained in the related application "A Method For Attaching Carbon Composites to Metallic Structures and Product Thereof," of W. N. Pratt, Ser. No. 07/173,792, now U.S. Pat. No. 4,907,733, assigned to the assignee of the present application, the contents or which application are incorporated herein by reference.

None of the patents discussed above is directed to a tensile test specimen and a method of fabricating the same wherein the specimen is or a carbon composite material and there is contemplated the provision of nickel plating on opposite ends along with hole walls in the ends so as to provide improved strength end portions for carrying out tensile testing on the specimen.

SUMMARY OF THE INVENTION

A method of fabricating a carbon composite tensile test specimen for high-temperature testing comprises drilling a plurality of holes in first and second end sections of the specimen and electroplating the end sections with nickel. The nickel-plated through holes in the end sections of the tensile test specimen prevent breakage of the ends in the jaws of the tensile testing apparatus. A standard-sized test specimen may be used in high-temperature testing with the jaws in the hot zone. The resistance to removal of the nickel plating from the specimen during testing can be improved by increasing the internal surface area of the through holes, or by extending the plating further down the specimen to where the cross section decreases, or by increasing the thickness of the nickel plating.

BRIEF DESCRIPTION OF THE DRAWING

A better understanding of the present invention may be realized from a consideration of the following detailed description, taken in conjunction with the accompanying drawing in which.

DESCRIPTION OF THE PREFERRED EMBODIMENT

The present invention provide methods of fabricating carbon composite tensile test specimens for use in high-temperature tests and includes the products fabricated thereby. Previously it has been found that, in high-temperature testing of carbon composite tensile specimens, an end will frequently break in the gripping jaws of the tensile testing apparatus. Also, it has previously been necessary to use longer-than-standard test specimens in high-temperature testing to keep the ends of the specimen out of the high-temperature zone. The method of fabricating high-temperature tensile test specimens from carbon composite materials described herein allows the use of standard-sized specimens and eliminates end breakage of the specimens in the jaws of the testing apparatus.

Figure 1:
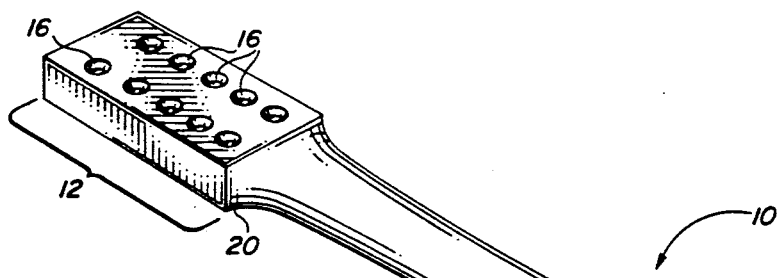
FIG. 1 is a perspective drawing of a carbon composite tensile test specimen fabricated by a method in accordance with the present invention.

In accordance with the present invention, a high-temperature carbon composite tensile test specimen as shown in FIG. 1 is fabricated. The first step in the procedure is to prepare first and second end portions 12 and 14 by drilling a plurality of holes in each. The holes 16 extend all the way through the tensile specimen at substantially right angles to the flattened surfaces of end portions 12 and 14. The holes 16 need not be arranged in any particular pattern. Next, end portions 12, 14 and through holes 16 are vapor blasted to clean and roughen the surfaces of the carbon composite material. This preparation of the surface makes for better adhesion of the nickel in the subsequent. plating step. The vapor blasting is done using water carrying fine alumina particles. A particle size of 280 mesh can be conveniently used.

Tensile test specimen 10 is then masked except for end portions 12, 14 and holes 16 before the plating process begins. Nickel is electroplated to a thickness of about 0.005 inch on the unmasked portions of the test specimen. Nickel sulfonate is a suitable type of plating solution to use in the plating step, details of which are well known in the art. The result, as illustrated in FIG. 1, is a tensile test specimen with nickel-plated end portions having pluralities of through holes 16 therein.

Since the adherence of the nickel plating 20 is probably largely mechanical, the surface area inside a through hole is probably a important factor in determining the strength of the reinforced end portions obtained by the present method. It follows that increasing the surface area inside a through hole 16 will provide greater strength.

This can be done, for example, by countersinking both sides of the hole before the plating step takes place.

Figure 2:
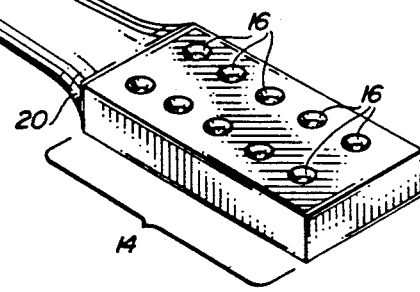
FIG. 2 is a top plan view of a carbon composite tensile test specimen with through holes having increased internal area.
Figure 2:
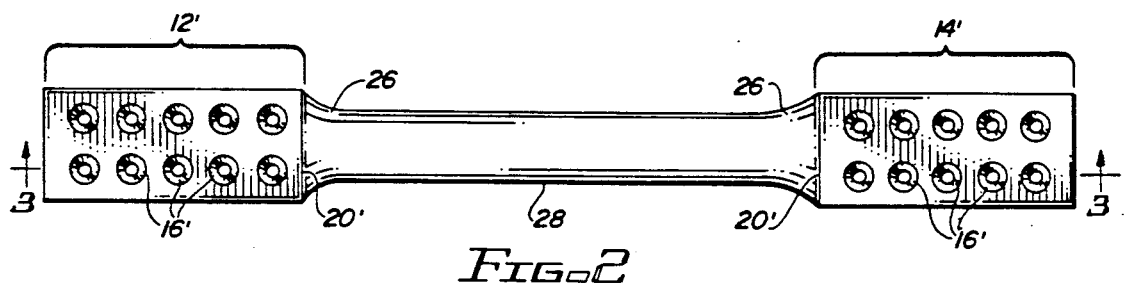

FIG. 2 is a top plan view of an alternative embodiment of a carbon composite tensile test specimen having strengthened end portions in accordance with the present invention. End portions 12' and 14' have pluralities of countersunk holes 16' in them. The countersinking of the through holes on both sides of each end portion serves to increase the internal surface area in the through holes and thus provide more holding strength from the plating of nickel.

Figure 3:
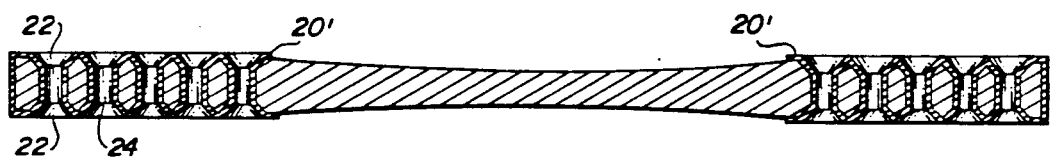
FIG. 3 is a side elevational view in section of the carbon composite tensile test specimen of FIG. 2, taken along the line 3—3.

FIG. 3 is a view in section of the specimen of FIG. 2. Each through hole 16' has a maximum cross section 22 at either exterior surface of the specimen and a minimum cross section 24 in between. Other ways of increasing the strength of the end portions include extending the plating 20'0 further to cover the adjacent portions 26 of the specimen where the cross sectional area is decreasing before attaining the reduced dimension of the central section 28 and also increasing the thickness of nickel plating.

Although there have been described above specific arrangements of a high-temperature tensile test specimen of a carbon composite material in accordance with the invention for the purpose of illustrating the manner in which the invention may be used to advantage, it will be appreciated that the invention is not limited thereto. Accordingly, any and all modifications, variations or equivalent arrangements which may occur to those skilled in the art should be considered to be within the scope of the invention as defined in the annexed claims.

What is claimed is:

1. A method of eliminating the breakage of specimen bars of carbon composite materials in the gripping jaws of a tensile test apparatus during high-temperature testing, comprising the steps of:
    a) drilling a plurality of holes through first and second end portions of a specimen bar of a carbon composite material on opposite sides of a longitudinal axis thereof and transverse to parallel surfaces of said bar which are gripped in said test apparatus during testing, there being a tensile test portion of said bar extending between said first and second end portions and contiguous therewith; and
    b) plating said first and second end portions of said bar including the circumferential walls of said holes with a selected metal to a predetermined thickness, said metal being nickel.

2. The method of claim 1 wherein step b) is accomplished by electroplating in a nickel sulfonate solution.

3. The method of claim 1 further comprising a penultimate step of increasing a surface area of circumferential wall in each said hole before plating.

4. The method of claim 3 wherein said step of increasing said surface area of circumferential wall in each said hole is accomplished by countersinking said hole from first and second sides.

5. The method of claim 1 wherein said plurality of holes in step a) consists of ten holes arranged in two parallel rows of five each.

6. A method of eliminating the breakage of specimen bars of carbon composite materials in the gripping jaws of a tensile test apparatus during high-temperature testing, comprising the steps of:
    a) drilling a plurality of holes through first and second end portions of a specimen bar of a carbon composite material on opposite sides of a longitudinal axis thereof and transverse to parallel surfaces of said bar which ar gripped in said test apparatus during testing, there being a tensile test portion of said bar extending between said first and second end portions and contiguous therewith; and
    b) plating said first and second end portions of said bar including the circumferential walls of said holes with a selected metal to a predetermined thickness;
    wherein said metal is nickel and said thickness is approximately 0.005 inch.

* * * * *